(12) United States Patent
Kubiak et al.

(10) Patent No.: US 8,758,272 B2
(45) Date of Patent: Jun. 24, 2014

(54) SYSTEMS, DEVICES, AND METHODS FOR MONITORING AN UNDER FOOT LOAD PROFILE OF A TIBIAL FRACTURE PATIENT DURING A PERIOD OF PARTIAL WEIGHT BEARING

(75) Inventors: Erik N. Kubiak, Salt Lake City, UT (US); Kylee North, Bountiful, UT (US); Emmon Johnny Chen, Sandy, UT (US); Jacob Joseph Hanson, Salt Lake City, UT (US); Zachary John Collins, Salt Lake City, UT (US); Robert W. Hitchcock, Sandy, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 12/833,214

(22) Filed: Jul. 9, 2010

(65) Prior Publication Data
US 2012/0010534 A1    Jan. 12, 2012

(51) Int. Cl.
*A61B 5/103* (2006.01)
*A61F 5/052* (2006.01)
*A61B 5/00* (2006.01)
*A61F 5/058* (2006.01)

(52) U.S. Cl.
CPC .............. *A61F 5/0585* (2013.01); *A61B 5/4842* (2013.01); *A61B 5/1036* (2013.01); *A61B 5/6812* (2013.01)
USPC ................. 600/592; 600/595; 73/172; 36/110

(58) Field of Classification Search
USPC ................. 600/587, 592, 595; 73/172; 36/110
See application file for complete search history.

(56) References Cited

U.S. PATENT DOCUMENTS

| | | | |
|---|---|---|---|
| 5,042,504 A * | 8/1991 | Huberti | 600/592 |
| 5,269,081 A * | 12/1993 | Gray | 600/592 |
| 5,357,696 A * | 10/1994 | Gray et al. | 600/592 |
| 5,359,791 A | 11/1994 | Prahl | |

(Continued)

FOREIGN PATENT DOCUMENTS

| | | |
|---|---|---|
| DE | 19804443 | 8/1999 |
| EP | 1494626 | 11/2006 |
| EP | 1519701 | 12/2009 |

OTHER PUBLICATIONS

Honeywell, Model 1865 Series Force/Pressure Tranducer, Apr. 2005, pp. 1-4.*

(Continued)

*Primary Examiner* — Rene Towa
*Assistant Examiner* — Emily Lloyd
(74) *Attorney, Agent, or Firm* — Workman Nydegger (57) ABSTRACT

Systems, devices, and methods for measuring an under foot load profile of a tibial fracture patient during a period of partial weight bearing are described. The system may include a walking boot cast. A housing, including an inner surface and an upper surface that cooperate to define an inner cavity, may be oriented with respect to a patient's tibia. The upper surface is slidably received within the inner cavity in a piston and cylinder configuration. The system may include a pressure sensor configured to monitor the load profile of a patient during the desired period of partial weight bearing. The pressure sensor may be located below the upper surface. The system may include a noncompressible force transmitter positioned within the inner cavity and at least partially encapsulating an upper portion of the pressure sensor to transmit pressure within the housing to the pressure sensor.

21 Claims, 7 Drawing Sheets

(56) References Cited

U.S. PATENT DOCUMENTS

| | | | |
|---|---|---|---|
| 5,452,527 A * | 9/1995 | Gaylord, Jr. | ............... 36/110 |
| 6,931,938 B2 | 8/2005 | Knirck | |
| 7,610,802 B2 * | 11/2009 | Clar et al. | ............... 600/592 |
| 8,280,681 B2 | 10/2012 | Vock | |
| 2002/0095105 A1 | 7/2002 | Jensen | |
| 2005/0172517 A1 | 8/2005 | Bledsoe | |
| 2005/0217142 A1 | 10/2005 | Ellis, III | |
| 2010/0280629 A1 | 11/2010 | Jung | |
| 2011/0054359 A1 | 3/2011 | Sazonov | |
| 2012/0010535 A1 | 1/2012 | Kubiak et al. | |
| 2012/0255160 A1 | 10/2012 | Boone | |

OTHER PUBLICATIONS

Hessert, Mary J. et al., "Foot Pressure Distribution During Walking in Young and Old Adults", May 19, 2005, BMC Geriatrics, vol. 5, pp. 1-8.*

Lawrence, T.L. et al., "Wireless In-Shoe Force System [For Motor Prosthesis]", Oct./Nov. 1997, Engineering in Medicine and Biology Society, vol. 5, pp. 2238-2241.*

Kaplan, Yonatan, "The Use of a New Biofeedback Insole Weight-Bearing Measuring Device in the Assessment and Rehabilitation of Soccer Players: A Case Study Review", 2007, Journal of Sports Science and Medicine, Suppl. 10, 5 pages.*

"The Quality In-Shoe Dynamic Pressure Measuring System", accessed on Jul. 30, 2013, http://www.novel.de/novelcontent/pedar 16 pages.*

Kubiak, et al., PCT/US2012/044966 International Search Report Dated Sep. 12, 2012.

Kubiak, et al., PCT/US2012/044966 Written Opinion Dated Sep. 12, 2012.

U.S. Appl. No. 13/178,314, Mail Date Nov. 27, 2012, Office Action.

North, Kylee "A Novel Load Sensor for Improving Tibial Fracture Outcomes", University of Utah Masters of Science Thesis, May 2010, 40 pages.

Authier, A. et al., "A Proof of Concept for a Wireless Ambulatory Weight Bearing Measurement System in Rehabilitation and Telerehabilitation Applications," Third IEEE International Conference on *Wireless and Mobile Computing, Networking and Communications*, Oct. 2007, pp. 73-80.

U.S. Appl. No. 13/178,314, Mar. 21, 2014, Notice of Allowance.

* cited by examiner

SYSTEMS, DEVICES, AND METHODS FOR MONITORING AN UNDER FOOT LOAD PROFILE OF A TIBIAL FRACTURE PATIENT DURING A PERIOD OF PARTIAL WEIGHT BEARING

BACKGROUND

1. The Field of the Disclosure

The present disclosure relates generally to systems, devices, and methods for measuring under foot load profiles. More particularly, the disclosure relates to systems, devices, and methods for monitoring an under foot load profile of a tibial fracture patient during a period of partial weight bearing (PWB).

2. The Relevant Technology

The tibia is the most commonly broken long bone in the body and requires between about ten weeks and about ten months to completely heal. The large number of complications associated with tibial fractures result in an annual direct cost for the United States of about $1.2 billion USD. The long rehabilitation times result in an annual indirect cost of about $95 billion USD mostly due to lost wages.

The mechanical environment experienced by the recovering bone is a major factor in fracture healing rate. In an attempt to produce an optimal mechanical environment to promote bone healing while reducing risk of complications, clinicians routinely prescribe PWB during tibial fracture rehabilitation.

The PWB prescription for a patient varies based on the extent of the injury and on the discretion of the clinician. This basis provides a vague guideline; little data has been collected to support that PWB prescriptions are effective at either promoting fracture healing or reducing the risk of complications. Additionally, the patients' tendency or ability to comply with the PWB prescription for the entire duration between follow up visits is unknown. Therefore, clinicians and researchers would greatly benefit from a load monitoring device that can continually track the PWB behavior of a patient between follow up visits, which may range from one day to typically two weeks apart.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

The present disclosure relates generally to systems, devices, and methods for measuring under foot load profiles. More particularly, the disclosure relates to systems, devices, and methods for monitoring an under foot load profile of a tibial fracture patient during a period of partial weight bearing (PWB).

An embodiment of a system for measuring an under foot load profile of a tibial fracture patient during a period of PWB is described. The system includes a walking boot cast configured to substantially immobilize the tibia and a housing oriented with respect to the patient's tibia. The housing includes an inner surface and an upper surface. The inner surface and the upper surface cooperate to define an inner cavity. The inner surface is substantially rigid and the upper surface is sized to be slidably received within the inner cavity in a piston and cylinder configuration. The system includes a pressure sensor configured to monitor the load profile of a patient during the desired period of PWB. The pressure sensor is located below the upper surface. The system also includes a noncompressible force transmitter positioned within the inner cavity of the housing and at least partially encapsulating an upper portion of the pressure sensor to transmit pressure within the housing to the pressure sensor.

In some embodiments, the pressure sensor is a miniature piezoelectric Wheatstone Bridge pressure sensor. The noncompressible force transmitter, in further embodiments, is a silicone gel.

The upper surface of the housing, in some embodiments, is connected to the inner surface of the housing by an elastomer. In further embodiments, the inner surface is formed from a urethane that is capable of being cast.

In some embodiments, the housing is located in a heel region and/or between a fourth and fifth metatarsal head portion of the walking boot cast. The housing, in further embodiments, includes an aperture to provide a reference pressure for determining the load profile.

A height of the housing, in some embodiments, is between approximately half and approximately one sixth of an axial dimension of the housing. In further embodiments, a major axial inner dimension of the housing is about 26 millimeters, a major axial outer dimension of the housing is about 30 millimeters, a height of the housing is about 7.5 millimeters, and a thickness of the inner surface of the housing is at least about 2 millimeters.

In some embodiments, the system includes a storage device configured to receive the measured load profile from the pressure sensor and the pressure sensor continuously monitors the load profile and transmits the load profile to the storage device. The storage device, in further embodiments, is located remote from the pressure sensor and the pressure sensor is configured for wireless communication with the storage device. In still further embodiments, the pressure sensor is located within a lower portion of the inner cavity of the housing.

An embodiment of a method for measuring an under foot load profile of a tibial fracture patient during a period of PWB is described. The method includes substantially immobilizing a tibia of a tibial fracture patient. A housing is oriented with respect to the patient's tibia. The housing includes an inner surface and an upper surface that cooperate to define an inner cavity. The inner surface is substantially rigid and the upper surface is sized to be slidably received within the inner cavity in a piston and cylinder configuration. A load is applied to the upper surface of the housing. The load profile generated by applying the load to the upper surface of the housing is monitored using a pressure sensor located below the upper surface and within a lower portion of the housing.

In some embodiments, the method includes storing the measured load profile from the pressure sensor. The method, in further embodiments, includes transmitting pressure from the load applied to the upper surface of the housing a noncompressible force transmitter.

Monitoring the load profile generated by applying the load to the upper surface of the housing, in some embodiments, includes continuously monitoring the load profile over a two-week period. In further embodiments, the method includes detecting the applied load prior to monitoring the load profile and after applying a load to the upper surface of the housing.

An embodiment of a method for treating a tibial fracture patient during a period of PWB is described. The method includes substantially immobilizing a tibia of a tibial fracture patient. A load is applied to an upper surface of a housing having an inner surface and an upper surface that define an inner cavity. The inner surface and the upper surface are substantially rigid. The upper surface is sized to be slidably received within the inner cavity in a piston and cylinder configuration. The load profile generated by applying the load to the upper surface of the housing is monitored using a pressure sensor located below the upper surface and within the inner cavity of the housing.

In some embodiments, the housing is located in a heel region and/or between a fourth and fifth metatarsal head portion of the walking boot cast and applying a load to the upper surface of the housing includes applying the load in the heel region and/or between the fourth and fifth metatarsal head portion of the walking boot cast. The monitoring of the load profile, in further embodiments, is done without recalibration after first applying the load to the upper surface of the housing.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

Although devices may be available that may analyze insole pressure, gait pathology, or plantar ulcer prevention in diabetic patients, these devices do not generally allow for continuous (greater than 1 hour) recording of the load placed on an injured limb. Often, such devices may be limited in part by the performance of their sensor technology. For example, capacitive resistors, ink based force-sensing resistors, pneumatically coupled systems connected to a pressure sensor, or force-sensing resistors may suffer from limitations such as hysteresis, creep nonlinearity, poor dynamic response, temperature effects, non-linearity, poor durability, or other limitations. Although insole pressure and/or gait analysis devices may be useful for their intended purposes, these systems may be limited in their ability to record the load placed on a limb for an extended period. Furthermore, these systems are generally very expensive.

To provide an economic solution to measuring the mechanical environment produced by Partial Weight Bearing (PWB), a need may exist for a durable, low cost load sensor that can record the load placed on an injured limb over a two-week period. The use of a micromachined silicon piezoresistive pressure sensor may provide an accurate and durable load sensor that is economic and capable of accurately measuring the normal loads experienced by the limb. Thus, a need may exist for systems, devices, and methods for monitoring an under foot load profile of a tibial fracture patient during a period of PWB. At least one embodiment of a system described herein may enable clinicians to understand how PWB may be used to direct tibial fracture outcomes, thereby reducing fracture healing time and complications.

A load profile may generally include an estimation of the amount of weight borne by a portion of the patient's lower-leg. For example, during a period of PWB the load profile may reflect aspects of the loading that may include maximum and minimum loads on the tibia, load duration, the total load over time, other aspects, or combinations thereof.

Figure 1:
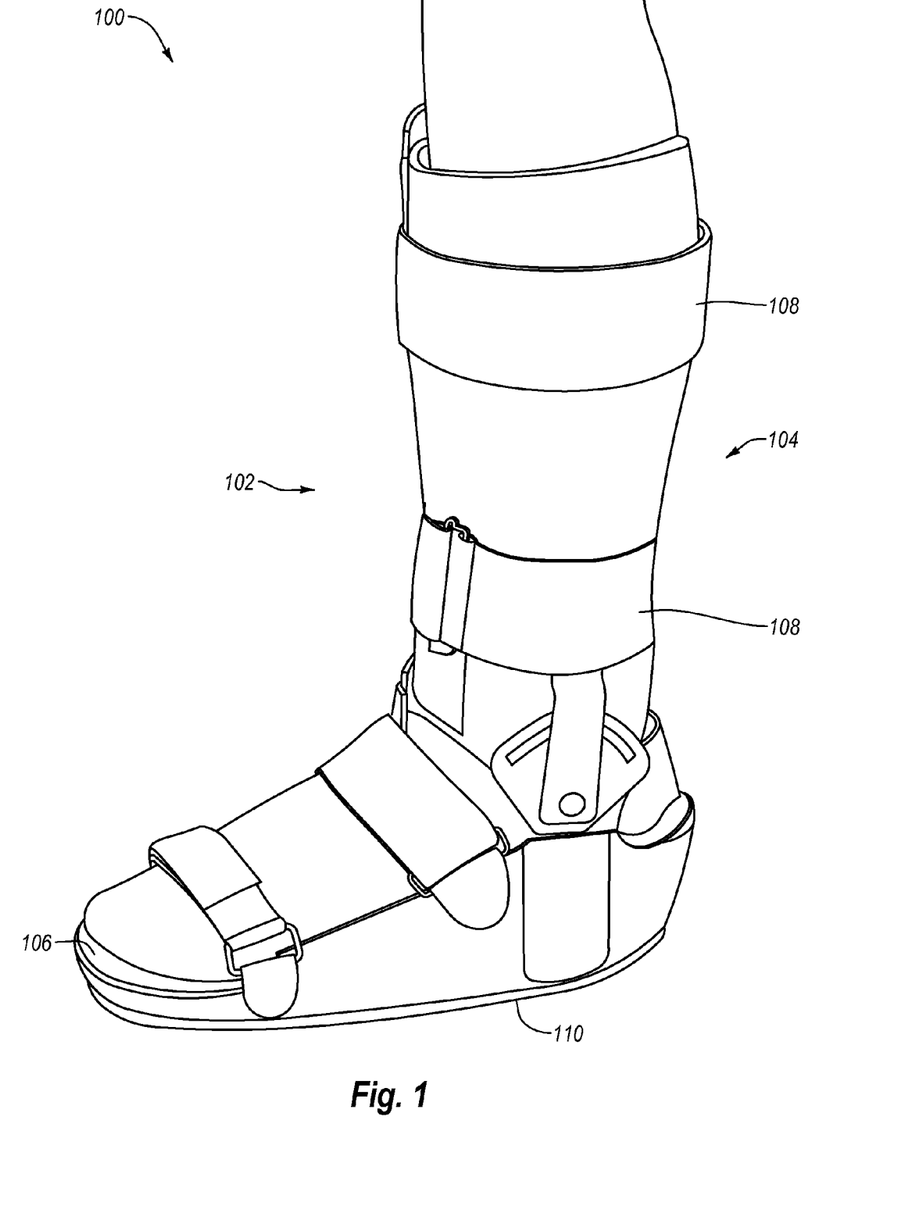
FIG. 1 illustrates a schematic representation of a system for measuring an under foot profile of a tibial fracture patient during a period of PWB according to an exemplary embodiment of the present disclosure.

FIG. 1 illustrates a schematic representation of a system 100 for measuring an under foot profile of a tibial fracture patient during a period of PWB according to an exemplary embodiment of the present disclosure. Generally after post-fracture edema or swelling has subsided, a tibial fracture patient may be prescribed a period of PWB. In order to stimulate osteogenesis while minimizing mechanical forces on the break, a PWB prescription may include the use of a walking boot cast 102. Alternatively, the PWB prescription may exclude the use of a lower-leg immobilizer 102 and/or may include the use of another orthotic device.

The walking boot cast 102 may include a force distribution section 104 and a foot bed 106. The patient's foot may be oriented with respect to the foot bed 106. The force distribution section 104 may be used to distribute forces generated by the patient's weight about the patient's lower leg. For example, retention straps 108 may facilitate retention and/or support of the patient's lower leg. Distributing the forces generated during a period of PWB may facilitate acceleration in the healing of the patient's fracture.

Walking boot cast 102 may include various features in addition to those described herein. For example, the walking boot cast 102 may include shock absorption features, positioning features, other features, or combinations thereof. One shock absorption feature may include modification of the tread 110. Rocker treads, softer materials, or other features may improve the tread 110.

Figure 2:
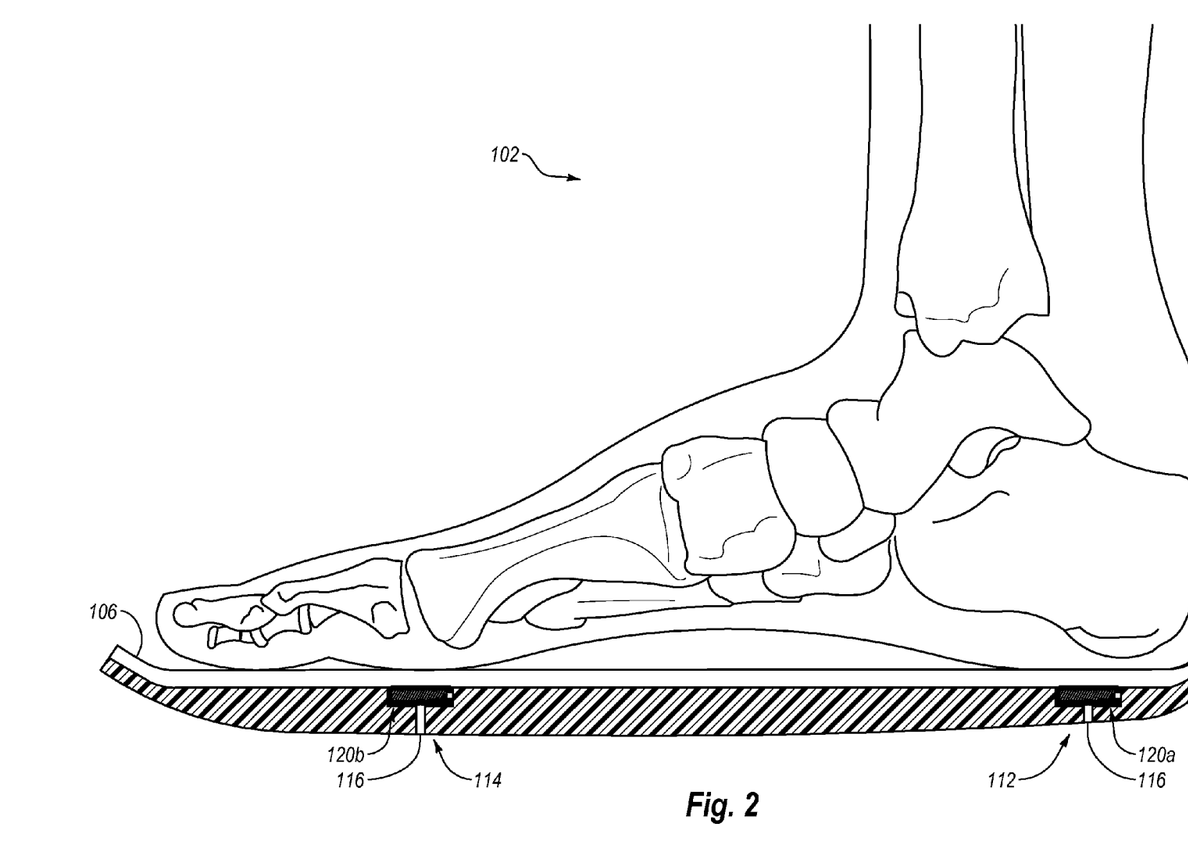
FIG. 2 illustrates a cutaway perspective view of the embodiment of the system of FIG. 1.

FIG. 2 illustrates a cutaway perspective view of the embodiment of the system 100 for measuring an under foot profile of a tibial fracture patient during a period of PWB of FIG. 1. Specifically, FIG. 2 generally illustrates the foot bed 106 of the walking boot cast 102. Although the foot bed 106 is illustrated as a part of the lower-leg immobilizer 102, in instances where the PWB prescription excludes the use of a lower-leg immobilizer 102, the foot bed 106 may be a part of another orthotic device. For example, another orthotic device may include a foot bed, such as a foot bed 106, but not a force distribution section, such as force distribution section 104 shown in FIG. 1.

In order to measure a load profile of a PWB patient, at least one load profile measuring device 120a, 120b may be located relative to the foot bed 106. Peak forces during walking are generally experienced at the heel of the foot during mid-stance and at the fourth and fifth metatarsal heads during toe off, thus, as illustrated in FIG. 2, a first load profile measuring device 120a may be located in the heel region 112 of the foot bed 106 and/or a second load profile measuring device 120b may be located in the ball region 114 (i.e. in the region of the 4th and 5th metatarsal heads) of the footbed 106. In other embodiments, a single load profile measuring device may be sized and/or configured to measure the load profile in both the ball region 114 and the heel region 112.

A reference aperture 116 is provided for each load profile measuring device 120a, 120b to facilitate a reference pressure measurement (i.e. atmospheric pressure), as illustrated in FIG. 2. The reference aperture 116 may include protective features such as a mesh and or other feature to limit passage of contaminants through the reference aperture 116.

The load profile measuring devices 120a, 120b may be integrally formed with the foot bed 106. In other embodiments, the foot bed 106 may include a pocket and/or aperture into which the load profile measuring devices 120a, 120b may be located and/or fixed.

Figure 3:
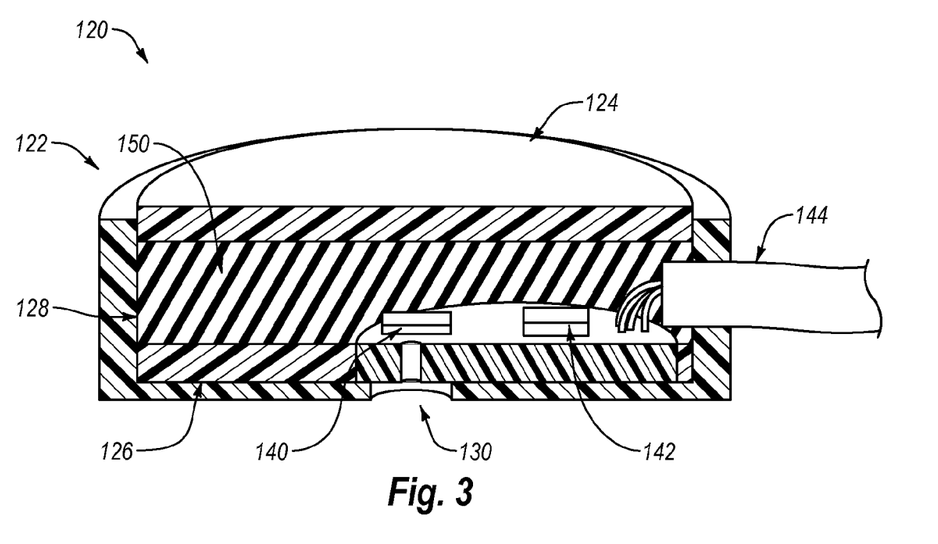
FIG. 3 illustrates a cutaway perspective view of the embodiment of the load profile measuring device of FIG. 2.

FIG. 3 illustrates a cutaway perspective view of the embodiment of a load profile measuring device 120 of FIG. 2. The load profile measuring device 120 may include a housing 122. The housing 122 may be inserted into a pocket and/or aperture of a foot bed, such as foot bed 106. In other embodiments, the housing 122 may be integrally formed with the foot bed.

The housing 122 may include an upper surface 124 and an inner surface 126 that may cooperate to define an inner cavity 128. As shown in FIG. 3, the upper surface 124 may be sized and/or configured to be slidably received within the inner cavity 128. In other words, the upper surface 124 and the inner cavity 128 may define a piston and cylinder configuration. The upper surface 124 and the inner cavity 128 are shown with a cylindrical shape.

The upper surface 124 may be flexibly connected to the inner surface 126. For example, the upper surface 124 may be connected to the inner surface 126 by an elastomer. The connection between the upper surface 124 and the inner surface 126 may be formed by coating, bonding, integrally forming, other connection mechanisms, or combinations thereof. Connecting the upper surface 124 with the inner surface 126 may seal the inner cavity 128 of the housing 122 to limit and/or prevent leakage and/or passage of contaminants.

The upper surface 124 and/or the inner surface 126 may be formed of a rigid material. For example, the upper surface 124 and/or the inner surface 126 may be formed of a rigid urethane that may be castable, such as Alumilite®, or other rigid materials. In the present embodiment, the upper surface 124 and the inner surface 126 are formed of the same material that may have the same general properties (i.e. flexibility). In other embodiments, the upper surface 124 and the inner surface 126 may be formed of the same or different materials having the same or different general properties. For example, the upper surface 124 may be formed of a flexible material while the inner surface 126 may be formed of a rigid material. In another example, the upper surface 124 may be formed of a first flexible material while the inner surface 126 is formed of a second flexible material.

In the present embodiment, the inner surface 126 of the housing 122 may include an aperture 130. The aperture 130 may correspond to the reference hole 116 described above in connection with FIG. 2.

The housing 122 may include a pressure sensor 140. The pressure sensor 140 may be configured to measure the load profile of the patient during the desired period of PWB.

The pressure sensor 140 may be in electronic communication with at least one signal conditioner 142. Signal conditioners 142 may include amplifiers, filters, input/output ports, microchips, other signal conditioners, or combinations thereof. The pressure sensor 140 may include an input/output 144. The input output may be connected to a data acquisition device and/or may be in electronic communication with at least one power source (not shown). A power source may include a battery power source, a direct power source, other power sources, or combinations thereof.

In the present embodiment, the pressure sensor 140 may include a miniature piezoresistive Wheatstone Bridge sensor. A Wheatstone Bridge sensor may provide favorable mechanical properties. For instance, a Wheatstone Bridge sensor may provide high linearity, high strength, high mechanical repeatability, high stiffness, little to no hysteresis, repeated cycling until failure, reduced variability between other Wheatstone Bridge sensors, other features, or combinations thereof. A Wheatstone Bridge sensor may be capable of monitoring loads over an extended period of time. For example, the Wheatstone Bridge sensor may be capable of monitoring loads over about a two week period of time.

Using a sensor with high linearity, little to no hysteresis, reduced variability between sensors, or combinations thereof may be desirable to reduce the amount of calibration required for each sensor. In other words, a sensor with high linearity, little to no hysteresis, reduced variability between sensors, or combinations thereof may result in a more accurate sensor that may not require individual calibration.

High strength, high mechanical repeatability (including repeated cycling until failure), and high stiffness in a pressure sensor may be desirable to reduce and/or prevent breakage due to stresses, fatigue, or other loading issues. For example, pressure sensors that are subject to stresses, fatigue, or other loading issues may experience wire breakage, damage to the device, or other problems that may affect the accuracy of the sensor.

Although at least one of the various mechanical properties described above may be desirable, these mechanical properties are not intended to limit the scope of the present disclosure. Rather, the claims must be used to determine the proper scope of the disclosure. In other words, in order to fall within the scope of the claims a pressure sensor need not provide any of the mechanical properties described above.

The pressure sensor 140 may be encapsulated by a force transmitter 150. As shown in FIG. 3, the pressure sensor 140 may abut the inner surface 126 of the housing 122 such that an upper surface of the pressure sensor 140 is encapsulated by the force transmitter 150. Additionally, the pressure sensor 140, the aperture 130, and the reference hole 116 described above in connection with FIG. 2 may be aligned to provide a reference pressure to the pressure sensor 140.

The force transmitter 150 may include a fluid or gel that may be selected to transmit pressure from the upper surface 124 and/or the inner surface 126 to the pressure sensor 140.

The compressibility of the force transmitter 150 may affect the uniformity of the transmission of forces to the pressure sensor 140. However, a compressible material may be acceptable in some situations for a force transmitter 150. For example, a minimally compressible material may still transmit forces to the pressure sensor 140, albeit nonuniformly. Examples of an acceptable fluid or gel for a force transmitter 150 may include a non-compressible silicone gel, other gels, or combinations thereof. After the force transmitter 150 is located within the inner cavity 128, a vacuum or other pressure may be applied the inner cavity 128.

Figure 4:
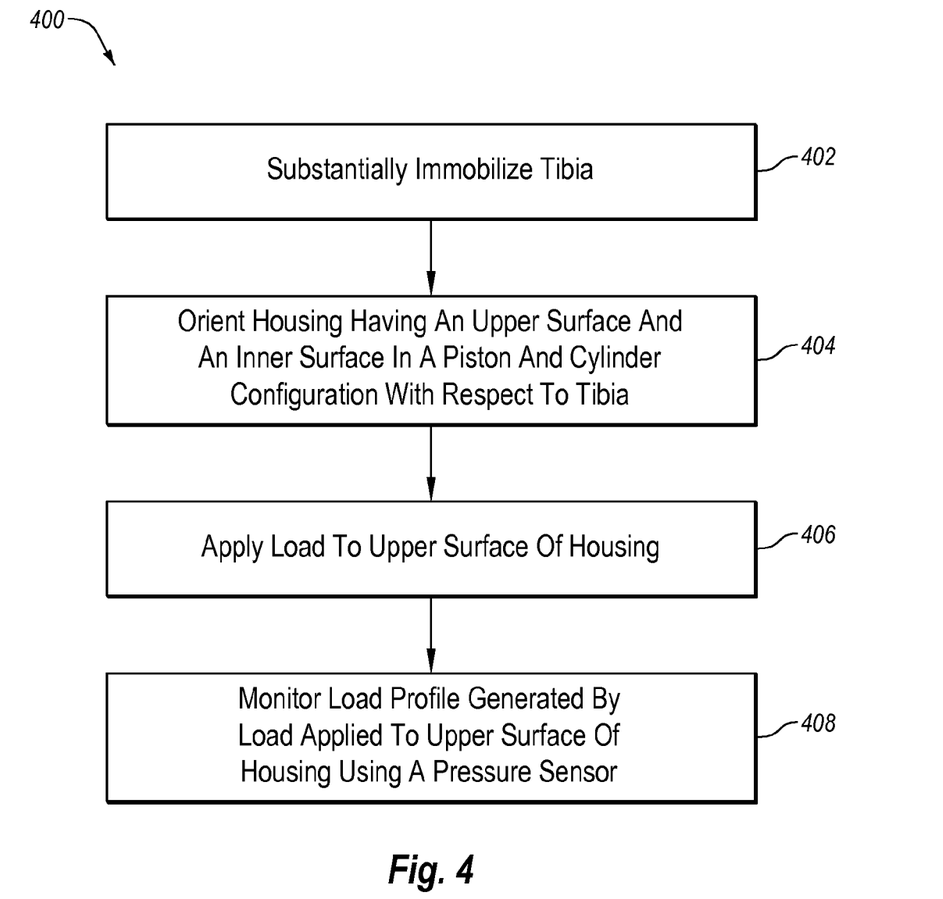
FIG. 4 illustrates an embodiment of a method for measuring an under foot load profile of a tibial fracture patient during a period of PWB.

FIG. 4 illustrates a method 400 for measuring an under foot load profile of a tibial fracture patient during a period of PWB. The method includes substantially immobilizing a tibia of a tibial fracture patient, as indicated by act 402. The tibia may be immobilized by a walking boot cast, such as the boot cast 100 described above.

The walking boot cast may include a housing, such as housing 122, that may be oriented, as indicated by act 404, with respect to the patient's tibia. For example, the housing 122 may be positioned, for example, in a heel region and/or a ball region of the patient's foot.

A load may be applied, as indicated in act 406, to the upper surface of the housing. For example, the patient may apply a load while standing, walking, sitting, or performing other activities. A load profile may be generated based on the applied load on the upper surface of the housing by a pressure sensor located below the upper surface and within a lower portion of the housing. This generated load profile may be monitored, as indicated by act 408. For example, the generated load profile may be continuously monitored over a two-week period.

The monitored load profile may be stored for later use. For example, a data acquisition unit may be used to store the monitored load profile. The monitored load profile may be used to provide feedback to the patient. For example, the data acquisition unit may notify the patient when they have exceeded a prescribed PWB allowance. Direct feedback may improve the outcomes of a patient that has been prescribed PWB.

A user interface may be used with the monitored load profile. For example, the peak loads, such as the maximum load experienced during ambulation, may be identified. These peak loads may be stored and/or used to provide direct feedback to the patient and/or clinician.

Monitoring the load profile may be performed without recalibration after first applying a load to the upper surface of the housing. For example, the pressure sensor may be configured to monitor the load profile without substantial drift.

The method 400 described above may also be used for treating a tibial fracture patient during a period of PWB. For example, the load profile data may be used to alter the initial PWB prescription. In other words, based on characteristics of the load profile, such as peak loads, cumulative loads, number of steps, other characteristics, or combinations thereof, the initial PWB prescription may be altered.

WORKING EXAMPLES

An embodiment of a load sensor was configured as a cylinder and piston design utilizing non-compressible silicone gel to generally uniformly transmit the pressure inside the cylinder to a piezoresistive Wheatstone bridge pressure sensor. In this example, the cylinder diameter remained constant and the pressure measured by the piezoresistive sensor was converted to load.

One corner of a piezoresistive pressure sensor die (a gauge-type microsensor—3000 series 15 psi piezoresistive pressure sensor manufactured by Merit Sensors, Salt Lake City, USA) was secured to a custom FR-4 printed circuit board (Circuit Graphics, Salt Lake City, USA) using UV-cure adhesive (3311 Loctite, Henkel Co., Dusseldorf, Germany). The piezoresistive sensor was electrically connected to the printed circuit board (PCB) by bonding aluminum-1% silicon alloy wire (Semiconductor Packaging Materials, Inc, Armonk, USA) between the pressure sensor die and the PCB using a 7476 D Manual Wedge bonder (West bond, Anaheim, USA). Wire bonds were reinforced with a small amount of acrylic-based, UV-cure adhesive (3311 Loctite). The microsensor was further secured and sealed to the printed circuit board with a UV-cure silicone (5248, Loctite) around the remaining base perimeter. On the PCB, the outputs of the piezoresistive sensor were connected to an AD8220 Instrumentation Amplifier (Analog Devices, Inc., Norword, USA) with a gain adjusting resistor, which was soldered to the PCB. In a portion of the studies, the instrumentation amplifier was not used, in which case the output of the piezoresistive sensor was electrically connected directly to the output leads of the PCB. To complete the circuitry, lead-out wires (AS 999-28-45J, Cooner Wires, Chatsworth, USA) were soldered to the PCB.

The sensor housing (including the upper plate) were fabricated from Alumilite® (Alumilite, Inc., Kalamazoo, USA), a two-part, rigid, castable urethane, poured into a silicone mold and allowed to cure for 5 minutes at room temperature. The assembled PCB was placed on the bottom of the sensor housing (ensuring that atmospheric reference holes are aligned), Alumilite® was poured into the sensor housing to seal the PCB and leadout wires to the sensor housing. Silbione HS firm gel LV 10-1 (Bluestar Silicones, East Brunswick, USA) was mixed according to manufacturers specifications and de-gassed for 30 minutes. The de-gassed gel was poured into the sensor housing, vacuumed again, and then placed in a mechanical convention oven for 15 minutes at 125° C. to cure the gel. To seal the load sensor assembly, the upper plate was coated in VST-50 silicone elastomer, placed on top of the sensor assembly, and then placed in the oven for an additional 10 minutes to cure the elastomer.

Pressure Linearity Testing

Sensor sensitivity, linearity, and hysteresis were characterized on eight load sensors by applying known air pressures prior to and after the application of the gel to assess the effects of the non-compressible silicone gel on the performance of the piezoresistive sensor. The eight tested load sensors were fabricated without amplifiers on the PCB. Sensors were powered with 5V, and output voltages were recorded using a precision datalogger (34970 A, Data Acquisition System manufactured by Agilent Technologies, Santa Clara, USA). Pressure was applied to the load sensor assembly with an ER3000 digital pressure controller (Tescom, Elk River, USA). An airtight seal was created around the top of the load sensor assembly and the pressure incremented and decremented in 7 kPa (1 psi) steps from 0 to 210 kPa (30 psi). After the no-gel condition was tested, 5 grams of the Silbione HS Firm Gel was added to each load sensor and the pressure testing was repeated.

Custom MatLab (MathWorks, Natick, USA) programs were used to analyze data from both the 34970 A DAS and ER3000. The average value for each pressure increment for each sensor was calculated for both the input pressure and output voltage data. This data was used to calculate, sensitivity, linearity and hysteresis. A Mann-Whitney U test for non-parametric data was used to determine statistical difference between the gel and non-gel condition for linearity.

Figure 5:
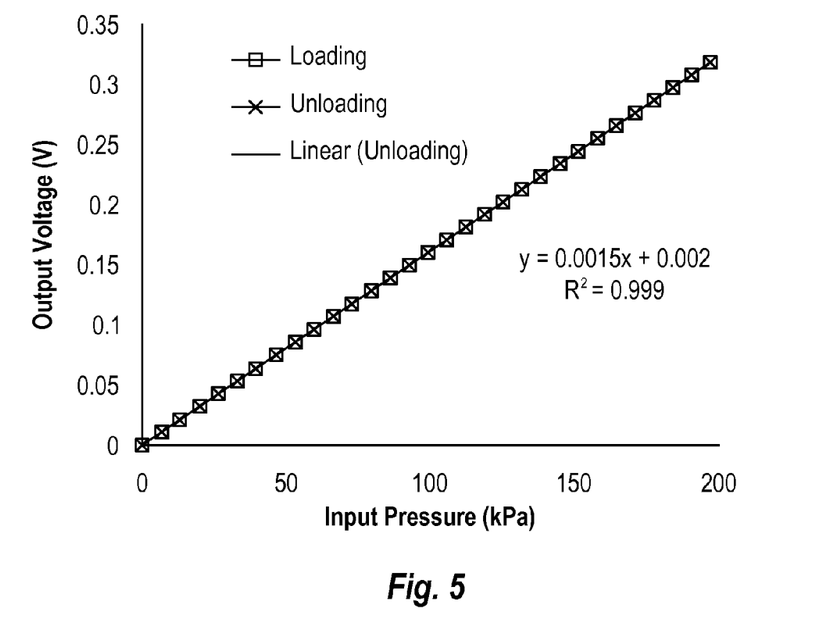
FIG. 5 illustrates the results from one of the sensors of a working example evaluated during pressure linearity testing.

The difference in sensitivities between the gel and no gel conditions were virtually undetectable using the described experimental setup. The measured sensitivity for both conditions and all eight sensors was about 0.0015 (SD 2.3×10-19) V/kPa. The average value of the correlation coefficient from the linear fit of the output voltage versus the input pressure graph for the no-gel and gel conditions were about 0.9998 (SD 3.5×10-4) and about 0.9999 (SD 8.3×10-5), respectively. A Mann-Whitney statistical test was used to compare the correlation coefficients between the gel and no-gel condition. There was virtually zero statistical difference between these conditions (P=0.774). FIG. 5 illustrates the results from one of the sensors evaluated during pressure linearity testing. There was no appreciable hysteresis between the loading and unloading curves. As there was no appreciable difference between sensor sensitivity and hysteresis, no statistics were performed.

Sensitivity Based Dimension Optimization

Nine different sensors assemblies of three inner diameters (about 20, 26, and 34 mm) and three heights (about 6, 9, 12 mm) were tested to evaluate the effect of the housing dimension on load sensor sensitivity. The sensors were supplied with a 5V input voltage (Agilent Technologies, Santa Clara, USA); the output voltage was read with National Instruments PCI-6221 DAQ card with a custom Labview program (National Instruments, Austin, USA). Loading of the sample was performed with a compression testing instrument (model 3342—Instron, Norwood, USA). The sensor was incrementally loaded 5 times in steps of 15 N from 0 to 195 N. The raw data from the Instron and the DAQ were analyzed using Matlab and Excel. The average voltage output from the sensor for each load was graphed against the applied load. A linear regression was used to calculate the sensitivity.

Figure 6:
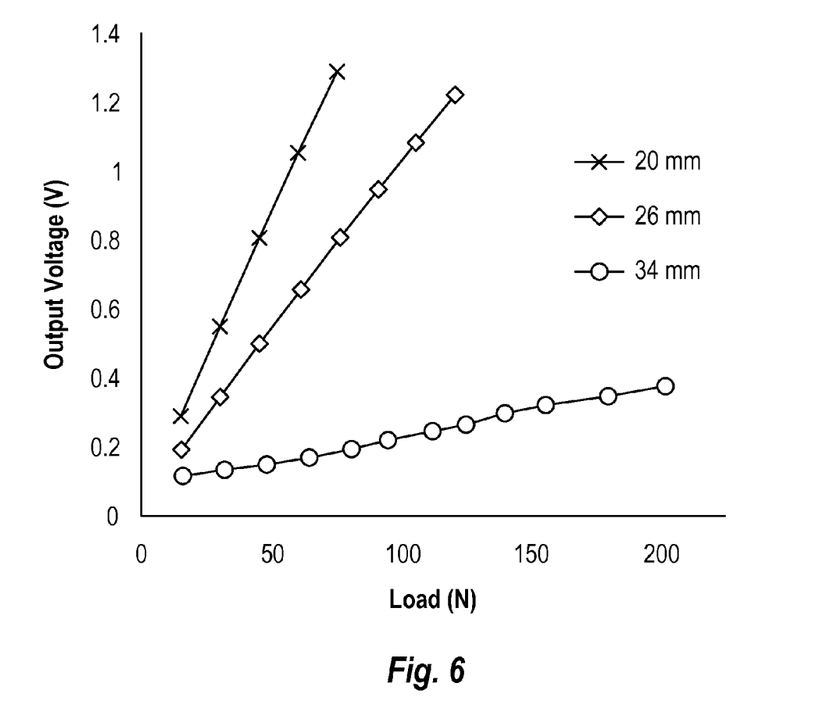
FIG. 6 illustrates the effects of varying the diameter of the housing of the working example on load sensor sensitivity with a sensor height of 9 mm.

The sensor housing dimensions had an effect on the sensitivity of the load sensor. The sensitivities ranged from about 0.0014 V/N with a housing diameter of about 34 mm to about 0.0164 V/N for a housing diameter of about 20 mm. While the housing diameter changed the sensor sensitivity by about 0.0063 V/N, the change in housing height had a less pronounced effect with an average change of about 0.0001 V/N. FIG. 6 displays the effects of varying diameter on load sensor sensitivity for three sensors with a sensor height of 9 mm.

Static Drift Testing

Figure 7:
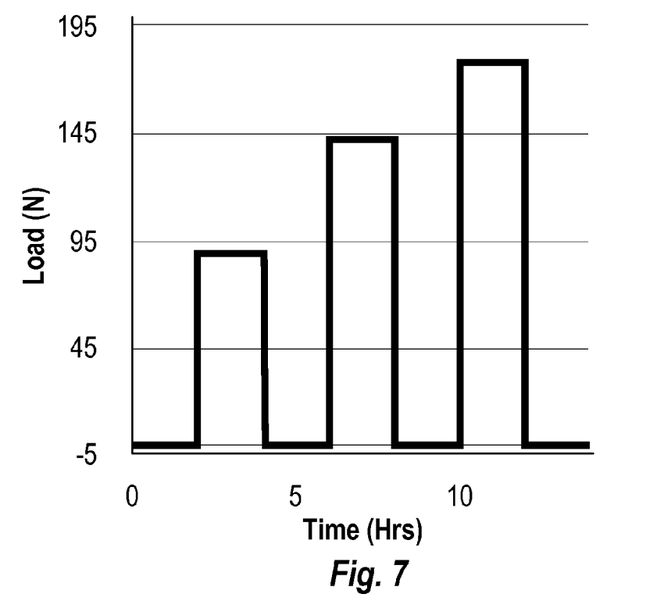
FIG. 7 illustrates the loads applied on the working example over time during a static drift test.

The results of the sensitivity testing motivated the final dimensions of the sensor housing. The inner diameter was about 26 mm, the outer diameter was about 30 mm, the thickness was about 2 mm, and the inner height was about 7.5 mm. Using these sensor housing dimensions, six new load sensors assemblies were prepared. The sensors were calibrated using the 3342 Instron. Input and output voltages, were recorded about every 30 seconds with the 34970A Agilent for the total about fourteen hours of testing. Three loads (about 90N, 140N, and 180N) were applied to the sensors for about two hours with about a two hour rest period in between each load, as shown in FIG. 7. The sensors were not rezeroed during this test in order to assess raw drift. The output voltages from the sensors were first normalized to the input voltage then converted to load values in Newtons using a calibration transfer function. Full scale drift percentage was calculated for both the return to zero and load conditions.

Figure 8:
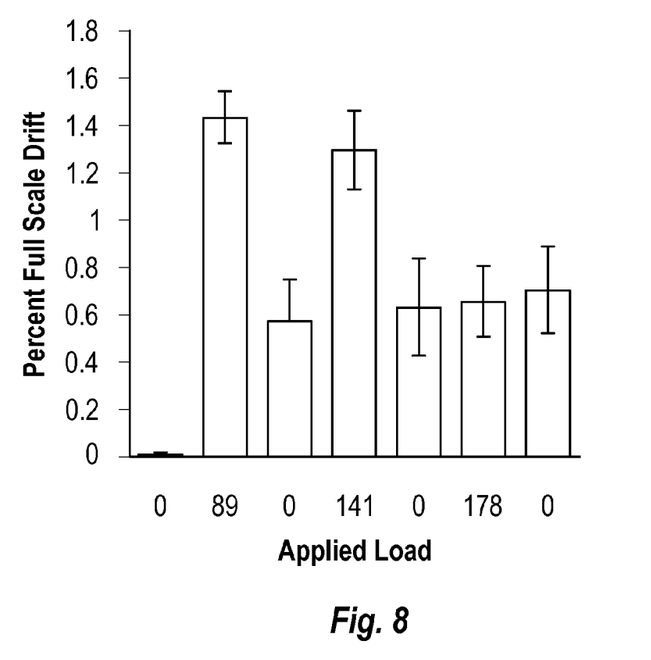
FIG. 8 illustrates the average drift for an approximately two hour period prior to, in between, and after loads were applied to various working example systems for measuring an under foot profile of a tibial fracture patient during a period of PWB.

The average 2-hour drift at loads of about 90, 140 and 180N was about 0.52% (SD 0.04), 0.46% (SD 0.06), and 0.23% (SD 0.05), respectively of full scale output (about 500 N). The average drift for the approximately two hour period prior to, in between and after the loads were applied was about 0% (SD 0.00), 0.20% (SD 0.06), 0.23% (SD 0.07), and 0.25% (SD 0.07), respectively of full scale output (about 500 N), as shown in FIG. 8.

Cyclic Loading

The load sensor was designed to function and maintain accuracy for a minimum of 14,000 cycles. Four of the load sensors used for drift testing were again used for cyclic testing. Cyclic testing was performed using a compression test instrument (Instron Model 1331) equipped with a 10 kN load cell and a NI SCB-68 DAQ interfaced with a custom LabView program to record from both the sensor and the Instron simultaneously. The Instron was programmed to cyclically load the sensors about 15,000 times from about 20-500 N at a frequency of 4 Hz. The sensors were not rezeroed during this test in order to assess the uncorrected effects of cyclic loading. Before the load sensors were cyclically loaded and after each set of about 5,000 cycles, a static load of about 400N was applied to the load sensor and the sensor output was recorded for about 5 seconds. The calibration transfer function used for the static drift testing was used to convert output voltage to load. The average load recorded by the sensor after each about 5,000 cycles was calculated by taking the mean of the entire approximately 5 seconds of recording.

Figure 9:
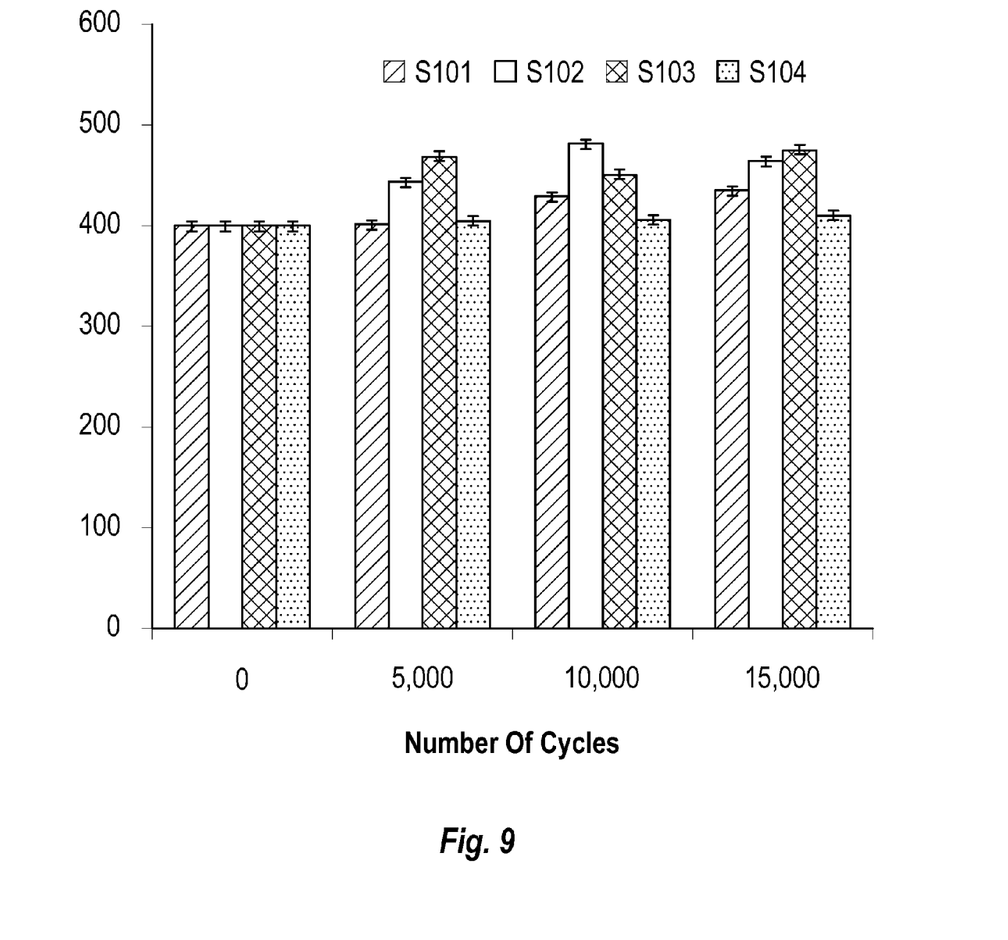
FIG. 9 illustrates the recorded sensor output after each set of 5,000 cycles for various working example systems for measuring an under foot profile of a tibial fracture patient during a period of PWB.

Cyclic testing showed varying amounts of drift between each recording period. The average drift for all the load sensors at the initial recording and after about 5,000, 10,000 and 15,000 cycles was about 0 (SD 0), 7 (SD 8), 10 (SD 8), and 11 (SD 7) % respectively. FIG. 9 displays the recorded sensor output after each set of 5,000 cycles for all the sensors. Sensor 104 had the lowest drift, reaching a maximum of about 2.0% after 15,000 cycles.

Treadmill Test in a Walking Boot Cast

To record the normal loads experience by the tibia during fracture recovery, the load sensor was designed to be placed in the heel region of a lower-leg immobilizer, which is generally worn during the entire rehabilitation period. Two subjects (one female about 50 kg, one male about 83 kg) walked on a treadmill for 30 steps at a speed of about 1.6 km/hr wearing the lower-leg immobilizer with the sensor placed under the heel. Two conditions were tested. The first was without the straps of the lower-leg immobilizer fastened. The second was with the straps securely fastened. A new load sensor was built and calibrated prior to testing. The load sensor's input and outputs were connected to NI USB-6210 DAQ (National Instruments, Austin, USA) which powered the sensor with about 5V DC and recorded the ratiometric voltage output at about 100 Hz sampling frequency. The load sensor voltage output was recorded for the entire duration of testing. The raw load sensor voltage output was converted to load using a linear calibration transfer function. Using a peak detection function in Matlab, the maximum and minimum tibial loads were extracted from the load profile. A paired student T-test was used to compare the peak loads between strap and no strap condition, and a non-paired student T-test was used to compare the peak loads between the two subjects; P values of less than about 0.05 determined statistical differences.

The average peak load for the male subject for the no strap and the strap condition were about 240(SD 13)N and about 215(SD 17)N respectively and about 234(SD 15)N and about 188(SD 14)N respectively for the female subject. The student T-test comparing the no strap and strap condition for both subjects led to the conclusion that there was a statistical difference between the strap and no-strap condition (P<about 0.05). The student T-test between the male and female subject for both conditions also led to the conclusion of a statistical difference between the male and female subjects in this study (P≤about 0.05).

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for measuring an under foot load profile of a tibial fracture patient during a period of partial weight bearing, the system comprising:
   a walking boot cast including a foot bed;
   a housing configured to be oriented with respect to the patient's tibia, said housing having an inner surface and an upper plate, said upper plate being aligned with respect to said foot bed, said inner surface and said upper surface plate cooperating to define an inner cavity, said inner surface being rigid, said upper surface plate being sized to be slidably received within said inner cavity in a piston and cylinder configuration with said upper plate acting as the piston and said inner surface acting as the cylinder, said upper plate being rigid;
   a pressure sensor configured to monitor the load profile of a patient during the desired period of partial weight bearing, said pressure sensor located below said upper plate; and
   a noncompressible gel positioned within said inner cavity of said housing and at least partially encapsulating an upper portion of said pressure sensor to transmit pressure within said housing to said pressure sensor.

2. The system of claim 1, wherein said pressure sensor is a miniature piezoelectric Wheatstone Bridge pressure sensor.

3. The system of claim 1, wherein said noncompressible gel is a silicone gel.

4. The system of claim 1, wherein said upper surface of said housing is connected to said inner surface of said housing by an elastomer as a sealed system, and wherein said noncompressible gel is degassed.

5. The system of claim 1, wherein said inner surface is formed from a rigid material.

6. The system of claim 1, wherein said housing is located in a heel region and/or between a fourth and fifth metatarsal head portion of said walking boot cast.

7. The system of claim 1, wherein said housing includes an aperture to provide a reference pressure for determining the load profile.

8. The system of claim 1, further comprising a storage device configured to receive the measured load profile from said pressure sensor and wherein the pressure sensor is configured to continuously monitor the load profile and to transmit the load profile to the storage device.

9. The system of claim 8, wherein the storage device is located remote from the pressure sensor and the pressure sensor being configured for wireless communication with the storage device.

10. The system of claim 1, wherein said pressure sensor is located within a lower portion of said inner cavity of said housing.

11. The system of claim 1, wherein the noncompressible gel is cured within the inner surface of the housing and the upper surface of the housing.

12. A method for measuring an under foot load profile of a tibial fracture patient during a period of partial weight bearing, the method comprising:
    orienting a housing with respect to a patient's tibia, said housing having an inner surface and an upper surface, said inner surface and said upper surface cooperating to define an inner cavity, said inner surface being rigid, said upper surface being sized to be slidably received within said inner cavity in a piston and cylinder configuration with said upper surface acting as the piston and said inner surface acting as the cylinder, said upper surface being rigid;
    applying a load to said upper surface of said housing;
    transmitting pressure from the load applied to said upper surface of said housing using a noncompressible gel, the noncompressible gel positioned within said inner cavity of said housing and at least partially encapsulating an upper portion of a pressure sensor to transmit pressure within said housing to said pressure sensor; and
    using a processor, monitoring the load profile generated by applying the load to said upper surface of said housing using said pressure sensor located below said upper surface and within a lower portion of said housing.

13. The method of claim 12, further comprising storing the measured load profile from said pressure sensor.

14. The method of claim 12, wherein the noncompressible gel is cured within the inner surface of the housing and the upper surface of the housing.

15. The method of claim 12, wherein monitoring the load profile generated by applying the load to said upper surface of said housing further comprises continuously monitoring the load profile over a two-week period.

16. A method for monitoring compliance of a tibial fracture patient during a period of partial weight bearing, the method comprising:
    applying a load to an upper surface of a housing having an inner surface and the upper surface, the inner surface and the upper surface defining an inner cavity, the inner surface and the upper surface being rigid, the upper surface being sized to be slidably received within the inner cavity in a piston and cylinder configuration with said upper surface acting as the piston and said inner surface acting as the cylinder;
    transmitting pressure from the load applied to said upper surface of said housing using a noncompressible gel, the noncompressible gel positioned within said inner cavity of said housing and at least partially encapsulating an upper portion of a pressure sensor to transmit pressure within said housing to said pressure sensor;
    using a processor, monitoring the load profile generated by applying the load to the upper surface of the housing using said pressure sensor located below the upper surface and within the inner cavity of the housing; and
    monitoring treatment of the patient based on at least a portion of the monitored load profile.

17. The method of claim 16, wherein the housing is located in a heel region of a walking boot cast and wherein applying a load to the upper surface of the housing further comprises applying the load in at least the heel region of the walking boot cast.

18. The method of claim 16, wherein the monitoring of the load profile is done without recalibration after first applying the load to the upper surface of the housing.

19. The method of claim 16, wherein the housing is located between a fourth and fifth metatarsal head portion of a walking boot cast and wherein applying a load to the upper surface of the housing further comprises applying the load at least between the fourth and fifth metatarsal head portion of the walking boot cast.

20. The method of claim 16, wherein monitoring the load profile comprises continuously monitoring the load profile over a two-week period.

21. The method of claim 16, further comprising adjusting treatment of the patient based on at least a portion of the monitored load profile.

* * * * *